May 18, 1943. W. F. SHANNON Plant Pat. 585
PEAR TREE
Filed March 20, 1942
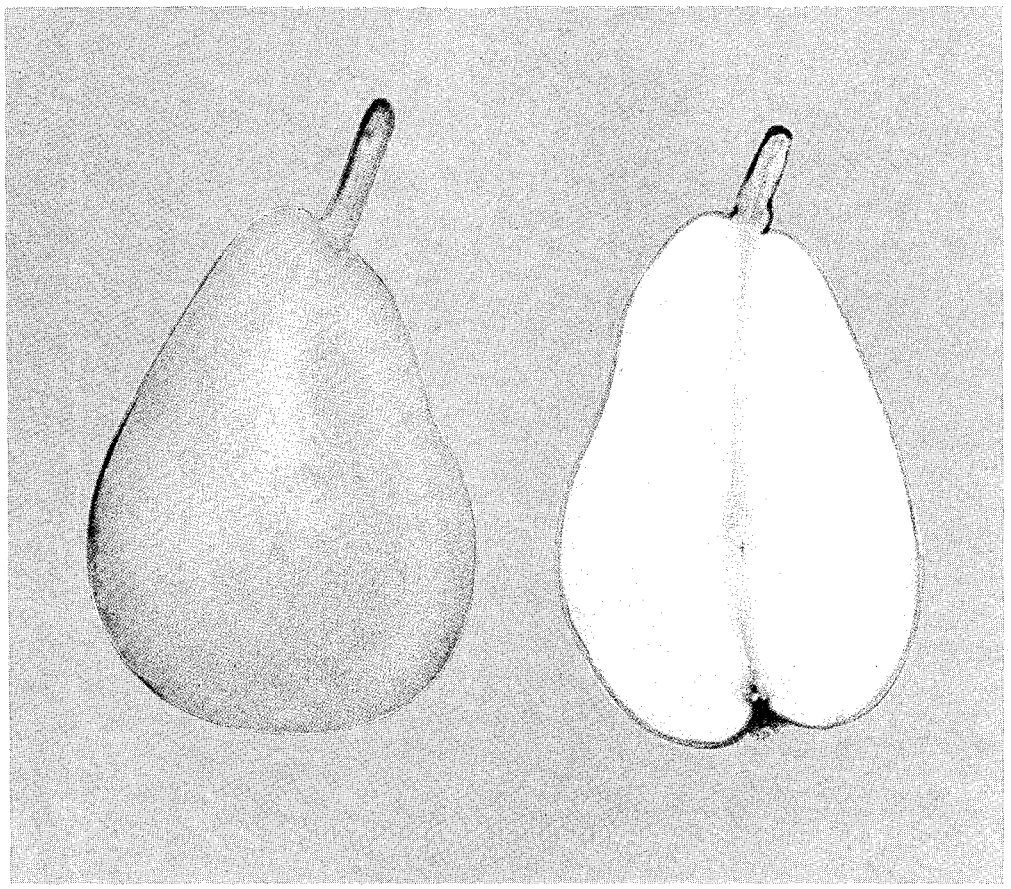
Inventor
W. F. Shannon
By Robert Robb
Attorneys Patented May 18, 1943

UNITED STATES PATENT OFFICE

585

PEAR TREE

Wesley F. Shannon, Hood River, Oreg., assignor to Stark Bro's Nurseries and Orchards Company, Louisiana, Mo.

Application March 20, 1942, Serial No. 435,593

1 Claim. (Cl. 47—62)

The present discovery relates to a new and distinct variety of pear tree, originating as a bud sport of the Gorham variety occurring on a tree now growing on my property.

The primary feature of distinction of this new pear resides in its solid, all-over golden russet color, as contrasted with that of its parent which is clear, pale yellow with very little russeting, except in the vicinity of the stem. This russet color is important from a commercial standpoint, because it prevents the pear from showing bruises and other injuries. In the present instance, the golden russet color can well be compared to the russet of the Beurré Bosc variety.

This new variety ripens about the same time as does its parent, or from three to four weeks after the Bartlett variety, and keeps from six weeks to two months longer in storage.

While in size, color and shape this new pear resembles the Bartlett, as well as the Gorham, its quality is superior. The flesh is white, tender, buttery and juicy, a combination which with a rich flavor and spicy aroma, makes it one of the best pears of the season.

Asexual reproduction of this new variety shows the foregoing characteristics come true to form and are established.

The following is a detailed description of the new variety, the color terminology used herein being in accord with Ridgway's Color Standard where indicated; otherwise with general dictionary meaning:

(Observations set forth made on specimens grown at Hood River, Oregon.)

*Tree*

Medium size; vigorous; upright; tall; round-topped; rapid growing; hardy; very productive; regular bearing.

Trunk: Medium stocky; medium smooth.

Branches: Slender; smooth; much branching; Grey, brownish when young.

Leaves: Length—2½ inches; width—2⅛ inches. Medium large; medium wide; medium long; ovate; abruptly pointed; medium thick; medium green; smooth.

*Margin.*—Finely serrate.

*Petiole.*—Medium long; medium thick. Length—1½ to 2 inches.

Flowers: Dates of first and full bloom—late mid-season, approximately with Anjou. Medium large; White.

*Fruit*

Maturity when described; eating ripe, middle of September.

Size: Uniform; axial diameter—3½ inches; transverse—2½ inches.

Form: Oblong, obtuse pyriform, often tapering to an acute neck.

*Cavity.*—Unsymmetrical; rounded; acute; furrowed; shallow and narrow.

Depth—$\frac{1}{16}$ inch.

Breadth—¼ inch.

Markings.—Sometimes flesh folds up around base of stem in a thick lip.

*Basin.*—Symmetrical; rounded; undulate; glabrous.

Depth—⅛ inch.

Breadth—½ inch.

Markings—Faint concentric circles.

Stem: Stout; glabrous.

*Length.*—¾ inch to 1 inch.

*Breadth.*—$\frac{3}{16}$ inch.

*Markings.*—Very small, inconspicuous, roughened areas.

Calyx: open; segments persistent; broadly lanceolate; length, ⅛ inch; separated at base; erect; reflexed from base at apex.

*Outer surface.*—Pubescent.

*Inner surface.*—Pubescent.

Eye: Medium size; open.

Skin: Thin; tender; smooth; dull; uniform solid russet.

*Dots.*—Conspicuous; many; small; submerged; circular.

*Color of dots.*—Greenish White.

*Distribution of dots.*—Uneven.

*Ground color.*—Clear Chalcedony Yellow.

*Color markings.*—Completely overspread Old Gold Russet (Ridgway).

*Color of markings.*—Old Gold Russet.

*Bloom.*—Wanting. *Scarfskin.*—Wanting.

*General color effect.*—A solid Golden Russet all-over color.

Flesh: Juicy.

*Color of flesh.*—White.

*Texture.*—Firm; tender; melting.

*Flavor.*—Mild; sweet; rich.

*Aroma.*—Wanting.

*Quality.*—Best.

Core: Distant.

*Bundle area.*—Small; cordate; symmetrical at base; alternate.

*Halves of area.*—Equal.

*Bundles.*—Yellowish tinge inconspicuous in one whorl.

*Core lines.*—Clasping; in cross section distinct.

*Carpellary area.*—Distinct; small.

*Calyx tube.*—Glabrous toward base; funnel form.

*Stem of funnel.*—Long; depth of tube to shoulder—$\frac{3}{16}$ inch; entire depth—$\frac{3}{8}$ inch.
*Styles.*—Present; fleshy at base; distinct toward base; glabrous toward base apex.
*Stamens.*—In one distinct whorl; marginal.
*Axillary cavity.*—Wanting.
*Seed cells.*—Axile; closed. Cell walls—approximate; thick; tough. Length—$\frac{1}{2}$ inch. Breadth—$\frac{1}{4}$ inch. Longitudinal section—ovate; acute. Surface—smooth. Cross section—narrow.

Seeds:
*Number perfect.*—Six.
*Number imperfect.*—Two
*Number in one cell.*—Two
*Length.*—$\frac{7}{16}$ inch.
*Color.*—Warm Blackish Brown (Ridgway).

Use: Market; local; dessert; culinary.

Keeping quality: Good.
*Number of days in ordinary storage.*—Six weeks.

Resistance to:
*Insects and disease.*—Good.

I claim:

A new and distinct variety of pear tree, characterized as to novelty by the all-over russet color of the skin of its fruit, the superior and keeping quality of the fruit, and the combination of the white, tender, buttery and juicy flesh with a rich flavor and spicy aroma, substantially as shown and described.

WESLEY F. SHANNON.